(12) United States Patent
Chun et al.

(10) Patent No.: US 10,584,371 B2
(45) Date of Patent: Mar. 10, 2020

(54) METHOD FOR LYOPHILIZATION OF COMPOSITION FOR MULTIPLE TARGET NUCLEIC ACID SEQUENCE AMPLIFICATION REACTION

(71) Applicant: SEEGENE, INC., Seoul (KR)

(72) Inventors: Jong Yoon Chun, Seoul (KR); Won Jun Oh, Seoul (KR)

(73) Assignee: SEEGENE, INC., Seoul (KR)

( * ) Notice: Subject to any disclaimer, the term of this patent is extended or adjusted under 35 U.S.C. 154(b) by 187 days.

(21) Appl. No.: 15/550,292

(22) PCT Filed: Feb. 12, 2016

(86) PCT No.: PCT/KR2016/001436
§ 371 (c)(1),
(2) Date: Aug. 10, 2017

(87) PCT Pub. No.: WO2016/129951
PCT Pub. Date: Aug. 18, 2016

(65) Prior Publication Data
US 2018/0023117 A1 Jan. 25, 2018

(30) Foreign Application Priority Data
Feb. 13, 2015 (KR) .................. 10-2015-0022306

(51) Int. Cl.
*C12Q 1/68* (2018.01)
*C12Q 1/6806* (2018.01)
*C12Q 1/686* (2018.01)

(52) U.S. Cl.
CPC ........... *C12Q 1/6806* (2013.01); *C12Q 1/686* (2013.01)

(58) Field of Classification Search
CPC .................................................. C12Q 1/6806

USPC ........................................................ 435/6.12
See application file for complete search history.

(56) References Cited

U.S. PATENT DOCUMENTS

| 2007/0110809 A1* | 5/2007 | Magagnoli ........... A61K 9/0019 |
| | | 424/486 |
| 2010/0209973 A1 | 8/2010 | Kim et al. .................... 435/91.2 |
| 2011/0159497 A1 | 6/2011 | Lee et al. ...................... 435/6.12 |

FOREIGN PATENT DOCUMENTS

| WO | WO 2007-005626 | 1/2007 | ............... C12Q 1/68 |
| WO | WO 2014-137093 | 9/2014 | ............... C12Q 1/68 |

OTHER PUBLICATIONS

International Search Report from corresponding PCT Application No. PCT/KR2016/001436 dated May 18, 2016.
Written Opinion of the International Searching Authority from corresponding PCT Application No. PCT/KR2016/001436 dated May 18, 2016.
Klatser et al., "Stabilized, freeze-dried PCR mix for detection of mycobacteria", Journal of Clinical Microbiology, vol. 36, No. 6, pp. 1798-1800 (1998).

\* cited by examiner

*Primary Examiner* — Jezia Riley
(74) *Attorney, Agent, or Firm* — Harness, Dickey & Pierce, P.L.C.

(57) ABSTRACT

The present invention relates to a method for lyophilizing a composition for multiple target nucleic acid sequence amplification reaction and a lyophilizate prepared by the method. The present method is very effective in lyophilizing a composition containing a high concentration of oligonucleotides. The lyophilizates prepared by the present invention exhibits excellent properties in terms of both sensitivity and specificity, equivalent performance capacity to conventional liquid formulation and furthermore remarkable storage stability. Accordingly, the lyophilizates prepared by the present invention would be very useful in diagnosis.

10 Claims, 4 Drawing Sheets

Fig. 1

| Group | A1 | A2 | B1 | B2 | C1 | C2 | D1 | D2 |
|---|---|---|---|---|---|---|---|---|
| Conc. of oligo-nucleotide (μM) | 5 | 5 | 10 | 10 | 20 | 20 | 40 | 40 |
| Conc. of Tween20 (%(w/v)) | 0.0057 | 0.057 | 0.0057 | 0.057 | 0.0057 | 0.057 | 0.0057 | 0.057 |

Fig. 2

A represents lyophilizate with 0.0057%(w/v) Tween 20.
B represents lyophilizate with 0.057%(w/v) Tween 20.
C represents lyophilizate with 0.11%(w/v) Tween 20.
D represents lyophilizate with 0.28%(w/v) Tween 20.
E represents lyophilizate with 0.57%(w/v) Tween 20.

Fig. 3

Groups with a primary drying for 48 hr

A represents lyophilizate with 0.0057%(w/v) Tween 20.
B represents lyophilizate with 0.057%(w/v) Tween 20.
C represents lyophilizate with 0.11%(w/v) Tween 20.

Fig. 4

Groups with a primary drying for 60 hr

A represents lyophilizate with 0.0057%(w/v) Tween 20.
B represents lyophilizate with 0.057%(w/v) Tween 20.
C represents lyophilizate with 0.11%(w/v) Tween 20.

METHOD FOR LYOPHILIZATION OF COMPOSITION FOR MULTIPLE TARGET NUCLEIC ACID SEQUENCE AMPLIFICATION REACTION

CROSS-REFERENCE TO RELATED APPLICATIONS

This application is a national phase application of PCT Application No. PCT/KR2016/001436, filed on 12 Feb. 2016, which claims priority to Korean Patent Application No. 10-2015-0022306, filed on 13 Feb. 2015. The entire disclosures of the applications identified in this paragraph are incorporated herein by reference.

FIELD OF THE INVENTION

The present invention relates to a method for lyophilizing a composition for multiple target nucleic acid sequence amplification reaction and a lyophilizate prepared by the method.

BACKGROUND OF THE INVENTION

Molecular diagnosis generally refers to nucleic acid analysis for detecting infection sources, genetic diseases, cancer and genetic variations of patients. It identifies presence of diseases or pathogens and likelihood of genetic disorders by detection or quantification of genetic materials from samples derived from human body such as blood, urine and saliva. The molecular diagnosis process generally includes in vitro amplification of nucleic acid molecules by amplification reactions such as polymerase chain reaction (hereinafter referred to as "PCR") and real-time PCR.

The most predominant process for nucleic acid amplification known as PCR is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al, (1985) Science 230, 1350-1354). Oligonucleotide primers used in PCR are designed to anneal to the opposite strand of DNA templates. The primers are extended by nucleic acid polymerase and the resulting extension product is served as a template strand for another primer in following reaction rounds. PCR amplification results in exponential increase of DNA fragments. For PCR, two primers, polymerase and nucleic acid template are typically utilized.

Nucleic acid amplification is a pivotal process for a wide variety of methods in molecular biology, such that various amplification methods have been proposed: LCR (Ligase Chain Reaction), GLCR (gap filling LCR), Q-beta (Q-beta replicase amplification), SDA (Strand Displacement Amplification), 3SR (self-sustained sequence replication), NASBA (Nucleic Acid Sequence-Based Amplification), TMA (Transcription Mediated Amplification) and RCA (Rolling-Circle Amplification). Novel and improved processes to a typical PCR protocol have been proposed.

Multiplex PCR was developed to simultaneously amplify multiple targets in a reaction and real-time PCR to qualitatively and quantitatively analyze amplification reactions of a target nucleic acid in a real-time manner.

Real-time PCR is one of PCR-based technologies in which a target nucleic acid is amplified together with measurement of the amplification reaction in a real-time manner, thereby detecting the target nucleic acid.

According to the typical PCR technologies, the reaction resultant is taken out after completion of amplification and then the presence or concentration of a target nucleic acid is measured. Unlikely, real-time PCR technologies are capable of is determining the presence and concentration of a target nucleic acid in a real-time manner. Real-time PCR technologies generally use labeled probes to be hybridized with a target nucleic acid. Methods involving hybridization between a labeled probe and a target nucleic acid include Molecular beacon method (Tyagi et al, Nature Biotechnology 14:303 (1996)), Hybridization probe method (Bernad et al, Clin Chem 46:147 (2000)) and Lux method (U.S. Pat. No. 7,537,886). TaqMan method widely used in the art utilizes hybridization of a dual-labeled probe and its cleavage reaction by 5' nuclease activity of DNA polymerase (U.S. Pat. Nos. 5,210,015 and 5,538,848).

The real-time detection methods are a homogeneous assay to perform amplification reaction and detection in a single tube, such that they require no additional operation and are free from carry-over contamination.

Enzymes are generally unstable in a liquid form at room temperature. Therefore, enzymes are usually stored in a lyophilized form or in a liquid form using stabilizer at −20° C. Although various storage strategies were proposed, activities of enzymes are very likely to be deceased due to frequent thawing and handling at room temperature.

Primers may form primer dimers by intra- or inter-strand primer annealing when stored in an aqueous environment, particularly at room temperature. In general, where a PCR reaction mixture is kept to stand for about 30 min at room temperature and then used for PCR amplification reaction, the production of a typical PCR product may be inhibited and sometimes may not be made. Furthermore, where a PCR reaction mixture is kept to stand for several hours to days at room temperature and then used for PCR amplification reaction, the production of a typical PCR product is very unlikely to occur.

Hitherto, most of PCR-based diagnosis products are supplied in the liquid form and have to be stored at −20° C., which are responsible for higher costs for transportation and storage.

A PCR process applied to various diagnosis technologies requires very elaborative techniques. The conventional PCR process is performed in such a manner that primers, polymerase, dNTPs, buffer and magnesium chloride are successively introduced into microtubes or multi-wall plate to prepare a reaction mixture and then nucleic acid template is introduced for amplification reaction. Some reagents such as polymerase and dNTPs have to be stored at −20° C. and other reagent such as primers and probes have to be stored at low temperature. As such, PCR-based diagnosis experimentations require dispensing small quantity of various materials which should be stored and handled under stringent conditions. Since the PCR-based diagnosis methods involve complicated and elaborative steps, very skillful technicians are demanded. It has been well known to one of skill in the art that PCR process is likely to produce false negative results due to experimentation errors and false positive results due to carry-over contamination.

To overcome such shortcomings, a PCR master mix in the dried form was suggested. The drying technologies are classified to two approaches. In the first approach, air drying at room temperature or high temperature under atmospheric pressure is performed. The second approach is lyophilization method in which samples are frozen and solvent molecules in the frozen samples are removed by sublimation. The lyophilization method comprises a freezing step and a drying step, which can remove solvent in a solid state to minimize structural changes during drying Lyophilization involves freezing a formulation, preferably by quick-frozen process. The frozen sample is then subject to sublimation of solvent in the frozen state at below freezing-point under high vacuum (a primary drying). Afterwards, a residual solvent is additionally removed with successively elevating temperatures (a secondary drying), providing a product in the form of crystal or powder. The final lyophilized product (lyophilizate) is in the form of porous cakes having the same shape and size as generally frozen materials.

Since the properties of lyophilizates are greatly affected by the shape and structure of cakes, high-quality lyophilizates require cakes with favorable shapes and structures. The lyophilizate cakes are required not to be disrupted because disrupted cakes are scarcely restored to possess their initial activities by reconstitution (rehydration). The physical structure of lyophilizate cakes should not be loose or soft.

The stability and post-reconstitution activity of lyophilizates are dependent greatly on properties of materials to be lyophilized and process of lyophilization. For successful lyophilization, various stabilizers and stabilization methods were proposed. Frank et al. suggested that carbohydrates as a cryoprotectant would improve stability and storage quality of lyophilizates (U.S. Pat. No. 5,098,893). However, the method has shortcomings in the senses that a drying step is performed at room temperature or elevated temperature around atmospheric pressure. American Type Culture Collection, Inc. commercialized lyophilized DNAs containing lactose as a cryoprotectant in the early 1980s. U.S. Pat. No. 5,955,448 discloses a stabilizing method in which biological samples having free amino, imino or guanidino side chains are incubated with non-reducing carbohydrate additive and inhibitor to Maillard reaction to prevent aggregation between free amino groups and reactive carbonyl groups. De Luca et al. proposed PCR lyophilized composition containing cellobiose as stabilizers (U.S. Pat. Appln. Pub. No. 2012/0064536). Perry et al. reported dried compositions containing fluorescent dye-linked nucleotides and Taq DNA polymerase substantially without glycerol (U.S. Pat. No. 7,407,747). Rajeev et al. suggested rotavirus vaccine compositions containing sucrose and glycine as additives (U.S. Pat. No. 8,795,686) and Fumitomo et al. suggested a lyophilization composition for reverse transcriptase containing trehalose, nucleic acid and metal salt (U.S. Pat. No. 5,935,834).

The real-time detection methods demand not only primers for amplification but also labeled primers or probes for detection. A PCR reagent mixture of multiplex PCR comprises at least two primer pairs for simultaneously amplifying multiple targets. In a composition for multiple target nucleic acid amplification such as multiplex PCR, oligonucleotides are contained at higher proportion or concentration in proportion to the number of the target. For simultaneously detecting multiple targets, the combination of real-time PCR and multiplex PCR (real-time multiplex PCR) has been suggested.

The compositions containing high-concentrated oligonucleotides are likely not to form lyophilizate cakes. Even though lyophilizate cakes are formed, the compositions containing high-concentrated oligonucleotides suffer from lyophilizate cake with unfavorable shapes and structures.

Accordingly, there is an urgent need to develop a novel method for lyophilizing compositions containing high-concentrated oligonucleotides for multiple target nucleic acid sequence amplification reaction.

Throughout this application, various patents and publications are referenced and citations are provided in parentheses. The disclosure of these patents and publications in their entirety are hereby incorporated by references into this application in order to more fully describe this invention and the state of the art to which this invention pertains.

SUMMARY OF THE INVENTION

The present inventors have made intensive researches to develop a novel approach for stably and effectively lyophilizing a composition for multiple target nucleic acid sequence amplification reaction. For accomplishing the research aims, the present inventors have made various attempts with adjusting types of additives and their concentration and lyophilization conditions such as time and temperatures such that the most appropriate approach is provided for a composition for multiple target nucleic acid sequence amplification reaction. As a result, the present inventors have found that polysorbate as additives exhibits excellent effects in lyophilizing compositions containing oligonucleotides (particularly, high-concentrated oligonucleotides) by inducing stable lyophilizate cake formation.

Accordingly, it is an object of this invention to provide a method for lyophilizing a composition for multiple target nucleic acid sequence amplification reaction.

It is another object of this invention to provide a lyophilizate of a composition for multiple target nucleic acid sequence amplification reaction.

It is still another object of this invention to provide a formulation for lyophilization.

It is further object of this invention to provide a use of an additive containing polysorbate in lyophilizing a composition for multiple target nucleic acid sequence amplification reaction.

It is still further object of this invention to provide a kit for multiple target nucleic acid sequence amplification reaction.

Other objects and advantages of the present invention will become apparent from the detailed description to follow taken in conjugation with the appended claims and drawings.

DETAILED DESCRIPTION OF THIS INVENTION

To accomplish the above-described objects, the present invention provides a method for lyophilizing a composition for multiple target nucleic acid sequence amplification reaction, comprising: (a) preparing a formulation comprising (i) the composition for multiple target nucleic acid sequence amplification reaction and (ii) an additive containing polysorbate; and (b) lyophilizing the formulation.

The present invention provides a lyophilizate of a composition for multiple target nucleic acid sequence amplification reaction prepared by the present method.

The present invention provides a formulation for lyophilization, comprising a composition for multiple target nucleic acid sequence amplification reaction and an additive containing polysorbate.

The present invention provides a use of an additive containing polysorbate in lyophilizing a composition for multiple target nucleic acid sequence amplification reaction.

I. Method for Lyophilizing Compositions for Multiple Target Nucleic Acid Sequence Amplification Reaction In one aspect of this invention, there is provided a method for lyophilizing a composition for multiple target nucleic acid sequence amplification reaction, comprising:

(a) preparing a formulation comprising (i) the composition for multiple target nucleic acid sequence amplification reaction and (ii) an additive containing polysorbate; and (b) lyophilizing the lyophilizing the formulation.

The present inventors have made intensive researches to develop a novel approach for stably and effectively lyophilizing a composition for multiple target nucleic acid sequence amplification reaction. For accomplishing the research aims, the present inventors have made various attempts with adjusting types of additives and their concentration and lyophilization conditions such as time and temperatures such that the most appropriate approach is provided for a composition for multiple target nucleic acid sequence amplification reaction. As a result, the present inventors have found that polysorbate as additives exhibits excellent effects in lyophilizing compositions containing oligonucleotides (particularly, high-concentrated oligonucleotides) by inducing stable lyophilizate cake formation.

The present inventors have firstly discovered that problems in lyophilized cake s formation are very likely to occur when concentrations of oligonucleotides in compositions become higher. The present invention can provide a novel approach for significantly overcoming such problems by using polysorbate as additives.

The present method will be described in more detail as follows:

Step (a): Preparation of a Formulation Comprising (i) the Composition for Multiple Target Nucleic Acid Sequence Amplification Reaction and (ii) an Additive Containing Polysorbate In the step (a), a formulation comprising (i) the composition for multiple target nucleic acid sequence amplification reaction and (ii) an additive containing polysorbate is prepared.

As used herein, the terms "formulation" refer to a mixture of two or more components such as compounds, elements and molecules. The formulation of the present invention is a formulation for lyophilization. The present formulation includes a solid formulation and liquid formulation, particularly, a liquid formulation. The liquid formulation refers to a formulation in a liquid state. The liquid formulation comprises any types of solution, any types of suspension with solid particles dispersed in a liquid, or a combination thereof, or an emulsion with liquid droplets dispersed in a liquid, or to a syrup. The liquid can be hydrophilic or lipophilic. A solution is considered as an embodiment of the present liquid formulation.

The formulation is characterized in that it comprises the composition for multiple target nucleic acid sequence amplification reaction and an additive containing polysorbate.

The preparation of the formulation may be performed by various methods. For example, such preparation may be carried out in such a manner that the composition for multiple target nucleic acid sequence amplification reaction and the additive are separately prepared and then mixed. Alternatively, the composition for multiple target nucleic acid sequence amplification reaction is mixed with an ingredient contained in the additive to provide the formulation.

The term used herein "the composition for multiple target nucleic acid sequence amplification reaction" refers to a subject to be lyophilized, including oligonucleotides containing primers for amplifying a target nucleic acid and enzymes (e.g., nucleic acid polymerase, nucleolytic enzyme and nucleic acid polymerase having nucleolytic activity) and other components for amplification (e.g., probes, buffers, metal ions, dNTPs and salts), but not limited to.

The term used herein "target", "target nucleic acid", "target nucleic acid sequence" or "target sequence" refers to a nucleic acid sequence of interest for analysis, detection or quantification. The target nucleic acid sequence comprises a sequence in a single strand as well as in a double strand. The target nucleic acid sequence comprises a sequence initially present in a nucleic acid sample as well as a sequence newly generated in reactions.

The target nucleic acid sequence may include any DNA (gDNA and cDNA), RNA molecules and their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glyoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

Where a mRNA is employed as starting material, a reverse transcription step is necessary prior to performing annealing step, details of which are found in Joseph Sambrook, et al, *Molecular Cloning, A Laboratory Manual*, Cold Spring Harbor Laboratory Press, Cold Spring Harbor, N.Y. (2001); and Noonan, K. F. et al., *Nucleic Acids Res.* 16:10366 (1988)). For reverse transcription, an oligonucleotide dT primer is hybridizable to poly A tail of mRNA, random primers or target-specific primers may be used.

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature. The target nucleic acid sequence may include known or unknown sequences.

The term used herein "multiple target nucleic acid sequence amplification reaction" refers to a reaction for simultaneously amplifying at least two target nucleic acid sequences in a reaction vessel.

A multitude of methods have been known for amplification of a target nucleic acid molecule, including, but not limited to, PCR (polymerase chain reaction), LCR (ligase chain reaction, see Wiedmann M, et al., "Ligase chain reaction (LCR)-overview and applications." PCR Methods and Applications 1994 February; 3(4):S51-64, U.S. Pat.

Nos. 4,683,195, 4,683,202), GLCR (gap filling LCR, see WO 90/01069, EP 439182 and WO 93/00447), Q-beta (Q-beta replicase amplification, see Cahill P, et aZ, Clin Chem., 37(9):1482-5(1991), U.S. Pat. No. 5,556,751), SDA (strand displacement amplification, see G T Walker et al., Nucleic Acids Res. 20(7):1691-1696(1992), EP 497272), NASBA (nucleic acid sequence-based amplification, see Compton, J. Nature 350(6313):91-2(1991)), TMA (Transcription-Mediated Amplification, see Hofmann W P et al., J Clin Virol. 32(4):289-93(2005); U.S. Pat. No. 5,888,779).) or RCA (Rolling Circle Amplification, see Hutchison C. A. et al., Proc. Natl Acad. Sci. USA. 102:1733217336(2005)). The amplification reaction in the present invention includes any type of the above-indicated amplification reactions.

According to an embodiment, the amplification of the target nucleic acid sequence in the present invention is PCR.

According to an embodiment, the composition for multiple target nucleic acid sequence amplification reaction comprises oligonucleotides and an enzyme.

The enzyme used in the present invention is selected from the group consisting of nucleic acid polymerase, nucleolytic enzyme, nucleic acid polymerase having nucleolytic activity and a combination thereof. Particularly, nucleic acid polymerase comprises DNA polymerase, including general nucleic acid polymerase, thermostable nucleic acid polymerase, recombinant nucleic acid polymerase, modified nucleic acid polymerase and Hot Start nucleic acid polymerase.

The oligonucleotides refer to a set for amplifying multiple target nucleic acid sequences, including ribonucleotides and deoxyribonucleotides.

The oligonucleotides comprise primers for amplification reaction. The primer refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The oligonucleotides may comprise at least one or at least two primer pairs for amplifying at least one or at least two target nucleic acid sequences. Particularly, the oligonucleotides contained in the composition for multiple target nucleic acid sequence amplification reaction comprises at least three (more particularly at least four, still more particularly at least five) primer pairs for amplifying at least three (more particularly at least four, still more particularly at least five) target nucleic acid sequences. According to an embodiment, the composition for multiple target nucleic acid sequence amplification reaction comprises oligonucleotides containing at least three primer pairs for amplifying at least three target nucleic acid sequences and an enzyme.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

According to an embodiment, the primer has a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, *Nucleic Acid Research*, 35:6e40(2007)).

According to an embodiment, the oligonucleotides used in the present invention may comprise an oligonucleotide for detection (e.g., probe and internal control sequence) as well as the amplification primer.

The probe used in the present invention refers to a single-stranded nucleic acid molecule comprising a portion or portions that are substantially complementary to a target nucleic acid sequence.

Particularly, the probe and primer are single-stranded deoxyribonucleotide molecules. The probes or primers used in this invention may be comprised of naturally occurring dNMP (i.e., dAMP, dGM, dCMP and dTMP), modified nucleotide, or non-natural nucleotide. For example, the probe and primer may comprise PNA (Peptide Nucleic Acid, see WO 92/20702) or LNA (Locked Nucleic Acid, see WO 98/22489, WO 98/39352 and WO 99/14226).

The target nucleic acid sequence is annealed to or hybridized with the primer or probe under hybridization, annealing or amplification conditions.

According to an embodiment, the oligonucleotides are present in the formulation in an amount of not less than 2 µM, 3 µM, 4 µM, 5 µM, 6 µM, 7 µM, 8 µM, 9 µM, 10 µM, 11 µM, 12 µM, 13 µM, 14 µM, 15 µM 16 µM, 17 µM, 18 µM, 19 µM, 20 µM, 21 µM, 22 µM, 23 µM, 24 µM, 25 µM, 26 µM, 27 µM, 28 µM, 29 µM or 30 µM. According to an embodiment, the oligonucleotides are present in the formulation in an amount of not more than 10 mM, 1 mM, 500 µM, 300 µM, 200 µM, 100 µM, 90 µM, 80 µM, 70 µM, 60 µM or 50 µM.

According to an embodiment, the oligonucleotides are present in the formulation in an amount of not less than 2 µM.

According to an embodiment, the oligonucleotides are present in the formulation in an amount of 2 µM-10 mM, 2 µM-1 mM, 2 µM-500 µM, 2 µM-100 µM, 2 µM-90 µM, 2 µM-80 µM, 2 µM-70 µM, 2 µM-60 µM, 2 µM-50 µM, 3 µM-50 µM, 4 µM-50 µM or 5 µM-50 µM.

The composition for multiple target nucleic acid sequence amplification reaction may further comprise other components in addition to the oligonucleotides and enzymes.

Biologically active molecules such as proteins and nucleic acid molecules exhibit optimal stability in relatively narrow pH range. Therefore, where the composition for multiple target nucleic acid sequence amplification reaction is prepared, a buffering agent is required to maintain the optimal pH for optimal activities.

The composition for multiple target nucleic acid sequence amplification reaction may comprise a suitable buffering agent, including, but not limited to, organic acid, glycine, histidine, glutamate, succinate, phosphate, acetate, citrate, Tris, HEPES, amino acids and a combination thereof. Particularly, the composition for multiple target nucleic acid sequence amplification reaction may comprise Tris buffer, more particularly Tris-HCl buffer.

Alternatively, the composition for multiple target nucleic acid sequence amplification reaction comprises no buffering agent. It is interesting that a lyophilized product prepared by the present method shows much higher stability when the composition with no buffering agent is used in the step (a).

The composition of the present invention may further comprise divalent metal ions as cofactors for allowing enzymes to show suitable activities. Particularly, the composition for multiple target nucleic acid sequence amplification reaction may comprise $MgCl_2$.

The composition for multiple target nucleic acid sequence amplification reaction may further comprise dNTPs and various salts.

The term used herein "additive" refers to materials or a set of materials used in lyophilizing the composition for multiple target nucleic acid sequence amplification reaction.

The additive used in this invention comprises polysorbate. The present inventors have found that polysorbate is considerably useful for successfully lyophilizing the composition for multiple target nucleic acid sequence amplification reaction containing a high concentration of oligonucleotides, which have been firstly suggested by the present inventors.

Polysorbate is one of surfactants or emulsifying agents widely used in pharmaceuticals and food additives and derived from PEGylated sorbitan esterified with fatty acid. Polysorbate is commercially available under the brand name of Canarcel™, Alkest™ or Tween™.

According to an embodiment, the polysorbate used in this invention is polysorbate 20, polysorbate 40, polysorbate 60 or polysorbate 80. The following numbers denote types of fatty acids. The numbers 20, 40, 60 and 80 represent monolaurate, monopalmitate, monostearate and monooleate, respectively.

More particularly, the polysorbate used in this invention is polysorbate 20 also referred to polyoxyethylene (20) sorbitan monolaurate or Tween 20.

The concentration of polysorbate may be dependent on concentrations of oligonucleotides in the composition for multiple target nucleic acid sequence amplification reaction. For example, the formulation may comprise polysorbate in an amount of at least 0.0012% (w/v), 0.0013% (w/v), 0.0014% (w/v), 0.0015% (w/v), 0.0025% (w/v) or 0.005% (w/v) based on 1 µM oligonucleotide.

According to an embodiment, the formulation may comprise polysorbate in an amount of not more than 10%, 5%, 4%, 3%, 2%, 1%, 0.9%, 0.8%, 0.7%, 0.6%, 0.5%, 0.4%, 0.3%, 0.2%, 0.1% or 0.05% (w/v) based on 1 µM oligonucleotides.

According to an embodiment, the formulation comprises polysorbate in an amount of 0.0012-0.9% (w/v), 0.0012-0.8% (w/v), 0.0012-0.7% (w/v), 0.0012-0.6% (w/v), 0.0012-0.5% (w/v), 0.0012-0.4% (w/v), 0.0012-0.3% (w/v), 0.0012-0.2% (w/v), 0.0012-0.1% (w/v) or 0.0012-0.05% (w/v) based on 1 µM oligonucleotides. More particularly, the formulation comprises polysorbate in an amount of 0.0012-0.5% (w/v), 0.0012-0.1% (w/v) or 0.0012-0.05% (w/v) based on 1 µM oligonucleotides.

Furthermore, the concentrations of polysorbate may be varied depending on other components than oligonucleotides. For example, polysorbate may be present in the formulation in an amount of not less than 0.01% (w/v), 0.02% (w/v) or 0.05% (w/v). Polysorbate may be present in the formulation in an amount of not more than 10% (w/v), 9% (w/v), 8% (w/v), 7% (w/v), 6% (w/v), 5% (w/v), 4% (w/v), 3% (w/v), 2% (w/v), 1% (w/v) or 0.5% (w/v).

According to an embodiment, polysorbate is present in the formulation in an amount of 0.01-5% (w/v), 0.01-4% (w/v), 0.01-3% (w/v), 0.01-2% (w/v), 0.01-1% (w/v) or 0.01-0.5% (w/v), more particularly 0.01-5% (w/v) or 0.01-0.5% (w/v).

According to an embodiment, the additive may comprise other component than polysorbate for lyophilization. For example, the additive may comprise surfactant and/or cryoprotectant.

Cryoprotectant is able to maintain protein structure during lyophilization, including, but not limited to, sugar alcohols such as alditol, manitol, sorbitol, inositol, polyethylene glycol and combinations thereof, and sugar acids such as aldonic acid, uronic acid, aldaric acid and combinations thereof.

Furthermore, cryoprotectant useful in this invention may comprise carbohydrates. Suitable carbohydrates are ketones or aldehydes having two hydroxyl groups. Carbohydrates may have ring or linear structures, including but not limited to aldose, ketose, amino sugar, alditol, inositol, aldonic acid, uronic acid, aldaric acid and combinations thereof.

Carbohydrates used in this invention may be monosaccharide, disaccharides (particularly, non-reducing disaccharides) and polysaccharides. Suitable carbohydrates includes, but not limited to, glyceraldehydes, arabinose, xylose, pentose, ribose, galactose, glucose, hexose, idose, mannose, talose, heptose, fructose, gluconic acid, sorbitol, lactose, mannitol, methyl alpha glucopyranoside, maltose, isoascorbic acid, ascorbic acid, lactone, arabinose, allose, altose, glucuronic acid, gluconic acid, glucaric acid, galacturonic acid, mannuronic acid, glucosamine, galactosamine, sucrose, trehalose, neuramic acid and derivates thereof. Suitable polysaccharides include, but not limited to, arabinan, fructan, fucan, galactan, galacturonan, glucan, mannan, xylan, levan, fucoidan, carrageenan, galactocarolose, pectin, pectic acid, amylose, pullulan, glycogen, amylopectin, cellulose, dextran, pustulan, chitin, agarose, keratin, chondroitin, dermatan, hyaluronic acid, xanthan gum and starch.

According to an embodiment, carbohydrate used in this invention is sucrose, glucose, lactose, maltose or trehalose.

According to an embodiment, cryoprotectant used in this invention is disaccharide or sugar alcohol. Particularly, disaccharide is a non-reducing disaccharide selected from the group consisting of sucrose, trehalose, maltose and lactose, and sugar alcohol is mannitol or sorbitol.

According to an embodiment, cryoprotectant used in this invention is trehalose.

According to an embodiment, the additive further comprises trehalose.

Trehalose may be present in the formulation in an amount of not less than 1% (w/v), 2% (w/v), 3% (w/v), 4% (w/v), 5% (w/v), 6% (w/v), 7% (w/v), 8% (w/v), 9% (w/v) or 10% (w/v). Furthermore, trehalose may be present in the formulation in an amount of not more than 30% (w/v), 25% (w/v), 24% (w/v), 23% (w/v), 22% (w/v), 21% (w/v), 20% (w/v) or 19% (w/v). According to an embodiment, trehalose may be present in the formulation in an amount of 5% (w/v) to 30% (w/v), for example, 5% (w/v) to 30% (w/v), 10% (w/v) to 30% (w/v), 10% (w/v) to 25% (w/v) or 10% (w/v) to 20% (w/v).

According to an embodiment, the additive further comprises polyethylene glycol (PEG). Polyethylene glycol or PEG represented by $H(OCH_2CH_2)_nOH$ (n is an integer of not less than 4) is condensation polymers of ethylene oxide and water. PEG may be commercially purchased under the brand name of Carbowax™. PEG is usually followed by numbers denoting a weight average molecular weight. For example, PEG 5,000 refers to polyethylene glycol with a total weight average molecular weight of about 5,000, PEG 12,000 to polyethylene glycol with a total weight average molecular weight of about 12,000 and PEG 20,000 to polyethylene glycol with a total weight average molecular weight of about 20,000.

Polyethylene glycol useful in this invention may be in a range of a total weight average molecular weight of 200-50,000, for example, 200-50,000, 200-30,000, 2,000-30, 000, 2,000-10,000, 4,000-10,000, 6,000-10,000 or 7,000-9,000. According to an embodiment, polyethylene glycol used in this invention is in a range of a total weight average molecular weight of 7,000-9,000, more particularly PEG 8000.

Polyethylene glycol may be present in the formulation in an amount of not less than 0.0001% (w/v), 0.001% (w/v), 0.01% (w/v), 0.1% (w/v), 0.2% (w/v), 0.3% (w/v), 0.4% (w/v), 0.5% (w/v), 0.6% (w/v), 0.7% (w/v), 0.8% (w/v), 0.9% (w/v) or 1% (w/v). Polyethylene glycol may be present in the formulation in an amount of not more than 10% (w/v), 9% (w/v), 8% (w/v), 7% (w/v), 6% (w/v), 5% (w/v), 4% (w/v), 3% (w/v) or 2% (w/v).

Polyethylene glycol may be present in the formulation in an amount of 0.0001% (w/v) to 10% (w/v), for example 0.0001% (w/v) to 10% (w/v), 0.0001% (w/v) to 5% (w/v), 0.0001% (w/v) to 2% (w/v), 0.001% (w/v) to 2% (w/v), 0.01% (w/v) to 2% (w/v) or 0.1% (w/v) to 2% (w/v).

According to an embodiment, the additive consists of or comprises polysorbate. According to an embodiment, the additive comprises not only polysorbate but also trehalose and/or polyethylene glycol.

Particularly, the additive comprises polysorbate 20, trehalose and polyethylene glycol 8,000.

According to an embodiment, the step (a) is performed by preparing a formulation comprising the composition for multiple target nucleic acid sequence amplification reaction containing oligonucleotides and an enzyme; and an additive containing polysorbate; wherein the oligonucleotides are present in the formulation in an amount of not less than 2 µM and polysorbate is present in the formulation in an amount of 0.01-5% (w/v).

According to an embodiment, the step (a) is performed by preparing a formulation comprising the composition for multiple target nucleic acid sequence amplification reaction containing oligonucleotides and an enzyme; and an additive containing polysorbate; wherein the oligonucleotides are present in the formulation in an amount of not less than 2 µM and polysorbate is present in the formulation in an amount of 0.0012-0.5% (w/v) based on 1 µM oligonucleotides.

According to another embodiment, the step (a) is performed by preparing a formulation comprising the composition for multiple target nucleic acid sequence amplification reaction containing oligonucleotides and an enzyme; and an additive containing polysorbate, trehalose and polyethylene glycol; wherein the oligonucleotides are present in the formulation in an amount of not less than 2 µM, polyethylene glycol is present in the formulation in an amount of 0.0001-10% (w/v), trehalose is present in the formulation in an amount of 5-30% (w/v), and polysorbate is present in the formulation in an amount of 0.01-5% (w/v).

According to another embodiment, the step (a) is performed by preparing a formulation comprising the composition for multiple target nucleic acid sequence amplification reaction containing oligonucleotides and an enzyme; and an additive containing polysorbate, trehalose and polyethylene glycol; wherein the oligonucleotides are present in the formulation in an amount of not less than 2 µM, polyethylene glycol is present in the formulation in an amount of 0.0001-10% (w/v), trehalose is present in the formulation in an amount of 5-30% (w/v), and polysorbate is present in the formulation in an amount of 0.0012-0.5% (w/v) based on 1 µM oligonucleotides.

According to still another embodiment, the step (a) is performed by preparing a formulation comprising the composition for multiple target nucleic acid sequence amplification reaction containing oligonucleotides and an enzyme; and an additive containing polysorbate, trehalose and polyethylene glycol; wherein the oligonucleotides are present in the formulation in an amount of 2-50 µM, polyethylene glycol is present in the formulation in an amount of 0.1-2% (w/v), trehalose is present in the formulation in an amount of 10-20% (w/v), and polysorbate is present in the formulation in an amount of 0.0012-0.5% (w/v) based on 1 µM oligonucleotides.

According to further embodiment, the step (a) is performed by preparing a formulation comprising the composition for multiple target nucleic acid sequence amplification reaction containing oligonucleotides and an enzyme; and an additive containing polysorbate, trehalose and polyethylene glycol; wherein the oligonucleotides are present in the formulation in an amount of 2-50 µM, polyethylene glycol is present in the formulation in an amount of 0.1-2% (w/v), trehalose is present in the formulation in an amount of 10-20% (w/v), polysorbate is present in the formulation in an amount of 0.0012-0.5% (w/v) based on 1 µM oligonucleotides, and the formulation comprises no buffering agent.

Step (b): Lyophilizing the Prepared Formulation

In the step (b), the formulation prepared in the step (a) comprising the composition for multiple target nucleic acid sequence amplification reaction and an additive containing polysorbate is lyophilized.

According to an embodiment, the lyophilization is performed by freezing the formulation and then drying the frozen formulation. The freezing and drying each may be performed through several steps each of which may be optionally carried out under reduced pressure.

Generally, a certain temperature and a range of temperatures for lyophilization process indicate a shelf temperature of a lyophilization apparatus. The shelf temperature refers to a controlled temperature of a coolant passing through a shelf is during lyophilization. The temperature of lyophilizate during a lyophilization process may be dependent on shelf temperature, chamber pressure and sublimation rate.

The lyophilization of the step (b) comprises a freezing step, a primary drying step and a secondary drying step.

According to an embodiment, the freezing is performed at temperature of not more than −20° C., for example, not more than −20° C., −25° C., −30° C., −35° C., −40° C., −45° C. or −50° C. According to an embodiment, the freezing is performed at temperature of not less than −80° C., for example, not less than −80° C., −70° C., −65° C., −60° C. or −55° C.

According to an embodiment, the freezing is performed at temperature of −20° C. to −80° C., −35° C. to −70° C., −35° C. to −65° C., −35° C. to −60° C., −40° C. to −60° C., −40° C. to −55° C., −45° C. to −60° C., −45° C. to −55° C. or −50° C. to −55° C.

According to an embodiment, the freezing is performed for not less than 1 hr, for example not less than 1 hr, 2 hr, 3 hr, 4 hr, 5 hr, 10 hr or 15 hr. According to an embodiment, the freezing is performed for not more than 96 hr, for example not more than 96 hr, 84 hr, 72 hr, 60 hr, 48 hr, 36 hr, 26 hr or 24 hr.

According to an embodiment, the freezing is performed for 1-96 hr, 2-84 hr, 5-72 hr, 10-60 hr, 10-48 hr, 10-36 hr, 10-26 hr, 12-48 hr or 12-24 hr.

According to an embodiment, the step (b) comprises freezing the formulation prepared in the step (a) at −20° C. to −80° C. for 1 hr to 96 hr.

More particularly, the step (b) comprises freezing the formulation prepared in the step (a) at −35° C. to −60° C. for 10 hr to 26 hr.

Still more particularly, the step (b) comprises freezing the formulation prepared in the step (a) at −40° C. to −55° C. for 12 hr to 24 hr.

The primary drying step is aimed to removal of solvent from the frozen formulation of the freezing step. The solvent removal is accomplished by sublimation. For promoting sublimation, the primary drying step is carried out with decreasing atmospheric pressure in drying chamber to become lower than vapor pressure of ice and heating to become higher temperature than that for the freezing step. The term "solvent" refers to a homogenous liquid material (inclusive of any water with which it may be combined) that is capable of at least partially dissolving material. The solvent used in the present invention may include, not limited to, water or cosolvent of water and other solvent (e.g., alcohol).

According to an embodiment, the temperature for the primary drying step is higher than that for the freezing step by not less than 3° C., for example not less than 3° C., 4° C., 5° C., 6° C., 7° C., 8° C., 9° C., 10° C., 15° C. or 20° C. According to an embodiment, the temperature for the primary drying step is higher than that for the freezing step by not more than 60° C., for example not more than 60° C., 55° C., 50° C., 45° C., 40° C., 35° C. or 30° C. According to an embodiment, the temperature for the primary drying step is higher than 3° C. to 60° C., 4° C. to 55° C., 5° C. to 50° C., 5° C. to 45° C., 10° C. to 40° C., 15° C. to 35° C. or 20° C. to 30° C. that for the freezing step.

According to an embodiment, the primary drying step is performed at temperature of not more than −15° C., for example not more than −15° C., −20° C., −25° C. or −30° C. According to an embodiment, the primary drying step is performed at temperature of not less than −60° C., for example not less than −60° C., −55° C., −50° C., −45° C., −40° C. or −35° C. According to an embodiment, the primary drying step is performed at temperature of −15° C. to −60° C., −15° C. to −55° C., −20° C. to −50° C., −20° C. to −45° C., −25° C. to −45° C., −25° C. to −40° C. or −30° C. to −35° C.

According to an embodiment, the primary drying step is performed under pressure of 0 mTorr to 200 mTorr or 50 mTorr to 100 mTorr.

The primary drying step is performed for a period of time sufficient to substantially remove all solvent from the frozen formulation. According to an embodiment, the primary drying step is performed for not less than 6 hr, for example, not less than 6 hr, 12 hr, 24 hr, 36 hr, 45 hr or 48 hr. According to an embodiment, the primary drying step is performed for not more than 96 hr, for example, not more than 96 hr, 84 hr, 75 hr, 72 hr or 60 hr. According to an embodiment, the primary drying step is performed for 6 hr to 96 hr, 12 hr to 84 hr, 24 hr to 75 hr, 36 hr to 75 hr, 45 hr to 75 hr, 48 hr to 72 hr or 48 hr to 60 hr.

According to an embodiment, the step (b) comprises performing a primary drying of the resultant of the freezing step at −15° C. to −60° C. for 6 hr to 96 hr.

More particularly, the step (b) comprises performing a primary drying of the resultant of the freezing step at −25° C. to −45° C. for 45 hr to 75 hr.

We have found that samples being subject to a primary drying for 60 hr exhibit better appearance of lyophilizate cake than those to a primary drying for 48 hr. Still more particularly, the step (b) comprises performing a primary drying of the resultant of the freezing step at −25° C. to −35° C. for 50 hr to 72 hr.

The secondary drying step is aimed to additional removal of solvent from the dried resultant of the primary drying step. The secondary drying step is carried out at temperature of not less than 0° C.

According to an embodiment, the temperature for the secondary drying step is not less than 0° C., for example not less than 0° C., 5° C., 10° C. or 15° C. According to an embodiment, the temperature for the secondary drying step is not more than 100° C., for example not more than 100° C., 50° C., 40° C., 30° C., 25° C. or 20° C. According to an embodiment, the temperature for the secondary drying step is in a range of 0° C. to 100, 5° C. to 50° C., 10° C. to 40° C., 10° C. to 30° C., 15° C. to 30° C., 18° C. to 22° C. or 15° C. to 25° C.

According to an embodiment, the secondary drying step is performed under pressure of 0 mTorr to 200 mTorr or 50 mTorr to 100 mTorr.

The secondary drying step is performed for a period of time sufficient to remove residual solvent from the dried resultant of the primary drying step. According to an embodiment, the final dried resultant of the secondary drying step has solvent content of not more than 10% (w/w), 9% (w/w), 8% (w/w), 7% (w/w), 6% (w/w), 5% (w/w), 4% (w/w), 3% (w/w), 2% (w/w), 1% (w/w), 0.8% (w/w), 0.6% (w/w), 0.5% (w/w), 0.2% (w/w) or 0.1% (w/w) based on the total weight of lyophilizate.

According to an embodiment, the secondary drying step is performed for not less than 0.1 hr, for example, not less than 0.1 hr, 0.5 hr or 1 hr. According to an embodiment, the secondary drying step is performed for not more than 48 hr, for example, not more than 48 hr, 36 hr, 24 hr, 12 hr, 6 hr, 4 hr, 3 hr or 2 hr. According is to an embodiment, the secondary drying step is performed for 0.1 hr to 48 hr, 0.1 hr to 36 hr, 0.5 hr to 48 hr, 0.5 hr to 24 hr, 0.5 hr to 12 hr, 0.5 hr to 6 hr, 0.5 hr to 4 hr, 0.5 hr to 3 hr or 0.5 hr to 2 hr.

According to an embodiment, the step (b) comprises performing a secondary drying of the resultant of the primary drying at 0° C. to 100° C. for 0.5 hr to 48 hr.

More particularly, the step (b) comprises performing a secondary drying of the resultant of the primary drying at 18° C. to 22° C. for 0.5 hr to 3 hr or 15° C. to 25° C. for 0.5 hr to 4 hr.

According to an embodiment, wherein the step (b) comprises: (i) freezing the formulation prepared in the step (a) at −20° C. to −80° C. for 1 hr to 96 hr; (ii) performing a primary drying of the resultant of the step (i) at −15° C. to −60° C. for 6 hr to 96 hr; and (iii) performing a secondary drying of the resultant of the step (ii) at 0° C. to 100° C. for 0.5 hr to 48 hr.

The lyophilized product (lyophilizate) prepared by the present method shows a residual solvent content of not more than 10% (w/w) based on the total weight of lyophilizate. According to an embodiment, the lyophilizate prepared by the present method shows a residual solvent content of 0.1% (w/w) to 10% (w/w) or 1% (w/w) to 10% (w/w) based on the total weight of lyophilizate.

II. Lyophilizate of Compositions for Multiple Target Nucleic Acid Sequence Amplification Reaction In another aspect of this invention, there is provided a lyophilizate of a composition for multiple target nucleic acid sequence amplification reaction prepared by the present method described above.

The lyophilizate of a composition for multiple target nucleic acid sequence amplification reaction refers to a resultant of lyophilization of a composition for multiple target nucleic acid sequence amplification reaction. The lyophilizate of present invention is characterized in that it is prepared by the method of present invention. The lyophilizate comprises a composition for multiple target nucleic acid sequence amplification reaction and an additive containing polysorbate. As the lyophilizate is prepared by the present method, it exhibits improved long-term stability even when the composition for multiple target nucleic acid sequence amplification reaction contains a high concentration of oligonucleotides. Therefore, the lyophilizate of the invention maintains its initial state or integrity in long-term storage and shows a high activity-recovery rate in reconstitution.

The lyophilizate of the invention may be prepared from a composition for multiple target nucleic acid sequence amplification reaction comprising no buffering agent. In such case, it is interesting that the stability of the lyophilizate becomes higher. The lyophilizate of the composition comprising no buffering agent may be reconstituted by using a suitable diluent such as buffering agents rather than water.

III. Formulation for Lyophilization

In still another aspect of this invention, there is provided a formulation for lyophilization, comprising a composition for multiple target nucleic acid sequence amplification reaction and an additive containing polysorbate.

The formulation for lyophilization refers to a mixed formulation comprising a subject to be lyophilized and an additive for lyophilization. The formulation of the present invention may include a solid formulation and liquid formulation. Particularly, the present formulation for lyophilization may be a liquid formulation.

The formulation for lyophilization is characterized in that it comprises the composition for multiple target nucleic acid sequence amplification reaction and the additive containing polysorbate.

Since the present formulation for lyophilization comprises the composition for multiple target nucleic acid sequence amplification reaction and the additive containing polysorbate used in the present lyophilization method described above, the common descriptions between them are omitted in order to avoid undue redundancy leading to the complexity of this specification.

The composition for multiple target nucleic acid sequence amplification reaction and the additive contained in the present formulation for lyophilization may be described with reference to descriptions in the present lyophilization method.

According to an embodiment, the formulation for lyophilization comprises oligonucleotides containing at least three primer pairs for amplifying at least three target nucleic acid sequences and an enzyme. The enzyme may be selected from the group consisting of nucleic acid polymerase, nucleolytic enzyme, nucleic acid polymerase having nucleolytic activity and a combination thereof. The oligonucleotides may be present in the present formulation in an amount of not less than 2 µM. The oligonucleotides and enzyme in the present formulation may be described with reference to descriptions in the present lyophilization method.

The additive in the formulation for lyophilization may further comprise a non-reducing disaccharide (e.g., trehalose). The additive may further comprise polyethylene glycol. The non-reducing disaccharide and polyethylene glycol in the present formulation may be described with reference to descriptions in the present lyophilization method. Polysorbate in the formulation for lyophilization may be polysorbate 20. Polysorbate may be present in an amount of 0.01-5% (w/v). Polysorbate may be present in an amount of 0.0012-0.5% (w/v) based on 1 µM oligonucleotides.

The formulation for lyophilization may comprise no buffering agent for amplification reaction, contributing to higher stability of lyophilizate.

The formulation for lyophilization excellently produces cake formation of lyophilizate, which leads to higher quality of lyophilizate and lower defective rate of products. Accordingly, the formulation for lyophilization leads to considerable long-term storage stability and activity-recovery rate in reconstitution of lyophilizate.

IV. Novel Use of Polysorbate

In further aspect of this invention, there is provided a use of an additive containing polysorbate in lyophilizing a composition for multiple target nucleic acid sequence amplification reaction.

When lyophilizates containing oligonucleotides are prepared, oligonucleotides affect lyophilizate cake formation. Particularly, a high concentration of oligonucleotides affects adversely the lyophilizate cake formation, which has been discovered by the present inventors. In this regard, the novel use of polysorbate for overcoming such problems would be novel and unobvious over any prior art.

V. Kit for Multiple Target Nucleic Acid Sequence Amplification Reaction

In still further aspect of this invention, there is provided a kit for multiple target nucleic acid sequence amplification reaction, comprising the lyophilizate prepared by the present method described above.

The present kit comprises the lyophilizate prepared by the present method described above.

The lyophilizate contained in the present kit comprises the composition for multiple target nucleic acid sequence amplification reaction and the additive containing polysorbate. The additive may further comprise trehalose and/or polyethylene glycol.

The lyophilizate in the present kit may be prepared by lyophilizing a formulation comprising the composition for multiple target nucleic acid sequence amplification reaction and the additive containing polysorbate. The composition for multiple target nucleic acid sequence amplification reaction comprises oligonucleotides containing at least three primer pairs for amplifying at least three target nucleic acid sequences and an enzyme. The oligonucleotides may be present in the formulation in an amount of not less than 2 µM. Polysorbate may be present in the formulation in an amount of 0.0012-0.5% (w/v) based on 1 µM oligonucleotides.

The lyophilizate in the present kit may be prepared by the steps of (i) freezing a formulation comprising the composition for multiple target nucleic acid sequence amplification reaction and the additive containing polysorbate at −20° C. to −80° C. for 1 hr to 96 hr; (ii) performing a primary drying of the resultant of the step (i) at −15° C. to −60° C. for 6 hr to 96 hr; and (iii) performing a secondary drying of the resultant of the is step (ii) at 0° C. to 100° C. for 0.5 hr to 48 hr. The lyophilizate thus prepared exhibits longer storage life for reconstitution and higher activity-recovery rate in reconstitution even when high concentrated oligonucleotides are present.

Since the lyophilizate in the present kit is prepared by the present method described above, the common descriptions between them are omitted in order to avoid undue redundancy leading to the complexity of this specification.

The present kit may optionally comprise one or more additional reagents. For example, the additional reagent is a suitable diluent for reconstitution of lyophilizates. The additional reagent may be in the form of solid or liquid. The additional reagent may be contained in a separated vessel from that for lyophilizate or in the same vessel in a distinctive manner or mixed manner. The present kit may optionally comprise instructions or manuals. The manual may be printed on or attached to a vessel of the kit, or may be contained as packaging components in kit.

As the present kit comprises the present lyophilizate of a composition for multiple target nucleic acid sequence amplification reaction, it is able to be stored and transported at room temperature. Furthermore, the present kit permits amplification experiments to be simplified, resulting in decrease in artifacts due to experimenters and more rapid experiments.

The lyophilizate of a composition for multiple target nucleic acid sequence amplification reaction contained in the present kit may comprise no buffering agent. In such case, a buffering agent for amplification reactions may be contained or used as diluents in the present kit.

The features and advantages of this invention will be summarized as follows:

(a) The present invention has been proposed based on novel findings in which high concentrated oligonucleotides are responsible for poor cake formation during lyophilization. The present inventors have discovered that polysorbate is able to overcome such shortcomings. Polysorbate contained as components of an additive for lyophilization is capable of preventing reduction of lyophilizate cake quality owing to high concentrated oligonucleotides, thereby leading to elevating quality of lyophilizates containing high concentrated oligonucleotides. The present lyophilizate with stably-formed cake shows longer storage life for reconstitution and higher recovery activity in the liquid form in reconstitution.

(b) The novel use of polysorbate as an additive for lyophilizing a composition for multiple target nucleic acid sequence amplification reaction is applicable to not only multiple target nucleic acid sequence amplification reaction but also lyophilization of various compositions containing high concentrated oligonucleotides. Furthermore, the novel use of polysorbate may be applied to compositions containing high concentrated oligonucleotides, enzyme, buffer, salt and various trace elements such as metal ions.

(c) In an embodiment, since the present lyophilizate is prepared together with all components for experiment purpose (e.g., detection of pathogens) in a single tube, experiments using it may become simplified, which contributes to decrease in artifacts due to experimenters, shortening experiment time and easier automation for experiments.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Preparation of Lyophilizates with Varying Oligonucleotide Concentrations To elucidate whether concentrations of oligonucleotides affect lyophilizate cake formation in lyophilizing compositions for multiple target nucleic acid sequence amplification reaction, lyophilizates of compositions for multiple target nucleic acid sequence amplification reaction were prepared by using varying concentrations of oligonucleotides.

The total oligonucleotide mixture (TOM) used in STI-7 Anyplex II (Seegene Inc., Korea) for detecting pathogens of sex-transmitted diseases was used as oligonucleotides.

To the composition for multiple target nucleic acid sequence amplification reaction containing oligonucleotides (TOM), Taq DNA polymerase, $MgCl_2$, dNTPs and Tris-HCl, the additive containing polysorbate (Tween 20), trehalose and polyethylene glycol was added, followed by mixing with water for preparing a formulation for lyophilization with the final volume of 30 µl. The preparation groups were divided to four groups depending on oligonucleotide concentrations. Each group includes two formulations comprising Tween 20 of 0.0057% (w/v) and 0.057% (w/v), respectively.

The prepared formulations for lyophilization comprising compositions for multiple target nucleic acid sequence amplification reaction were summarized in Table 1.

TABLE 1

| Formulation for lyophilzation | | A1 | A2 | B1 | B2 | C1 | C2 | D1 | D2 |
|---|---|---|---|---|---|---|---|---|---|
| Composition for amplification reaction | TOM (µM) | 5 | 5 | 10 | 10 | 20 | 20 | 40 | 40 |
| | Taq DNA polymerase (unit) | 1 | 1 | 1 | 1 | 1 | 1 | 1 | 1 |
| | $MgCl_2$ (mM) | 2.5 | 2.5 | 2.5 | 2.5 | 2.5 | 2.5 | 2.5 | 2.5 |
| | dNTP (mM) | 0.3 | 0.3 | 0.3 | 0.3 | 0.3 | 0.3 | 0.3 | 0.3 |
| | Tris-HCl (mM) | 20 | 20 | 20 | 20 | 20 | 20 | 20 | 20 |
| Additive | Tween20 (% (w/v)) | 0.0057 | 0.057 | 0.0057 | 0.057 | 0.0057 | 0.057 | 0.0057 | 0.057 |
| | Trehalose (% (w/v)) | 18.15 | 18.15 | 18.15 | 18.15 | 18.15 | 18.15 | 18.15 | 18.15 |
| | Polyethylene glycol (% (w/v)) | 1.65 | 1.65 | 1.65 | 1.65 | 1.65 | 1.65 | 1.65 | 1.65 |
| Proportion of Tween20 based on 1 µM TOM (% (w/v)) | | 0.00114 | 0.0114 | 0.00057 | 0.0057 | 0.000285 | 0.00285 | 0.000142 | 0.00142 |

The prepared formulations for lyophilization were lyophilized using VirTis Advantage plus (Warminster, Pa.). The formulations for lyophilization were frozen at −55° C. for 24 hr. Then, they were primarily dried at −30° C. for 48 hr and then secondarily dried at 20° C. for 30 min for preparing lyophilizates of compositions for multiple target nucleic acid sequence amplification reaction. For lyophilization, a pressure of 100 mTorr was applied.

Figure 1:
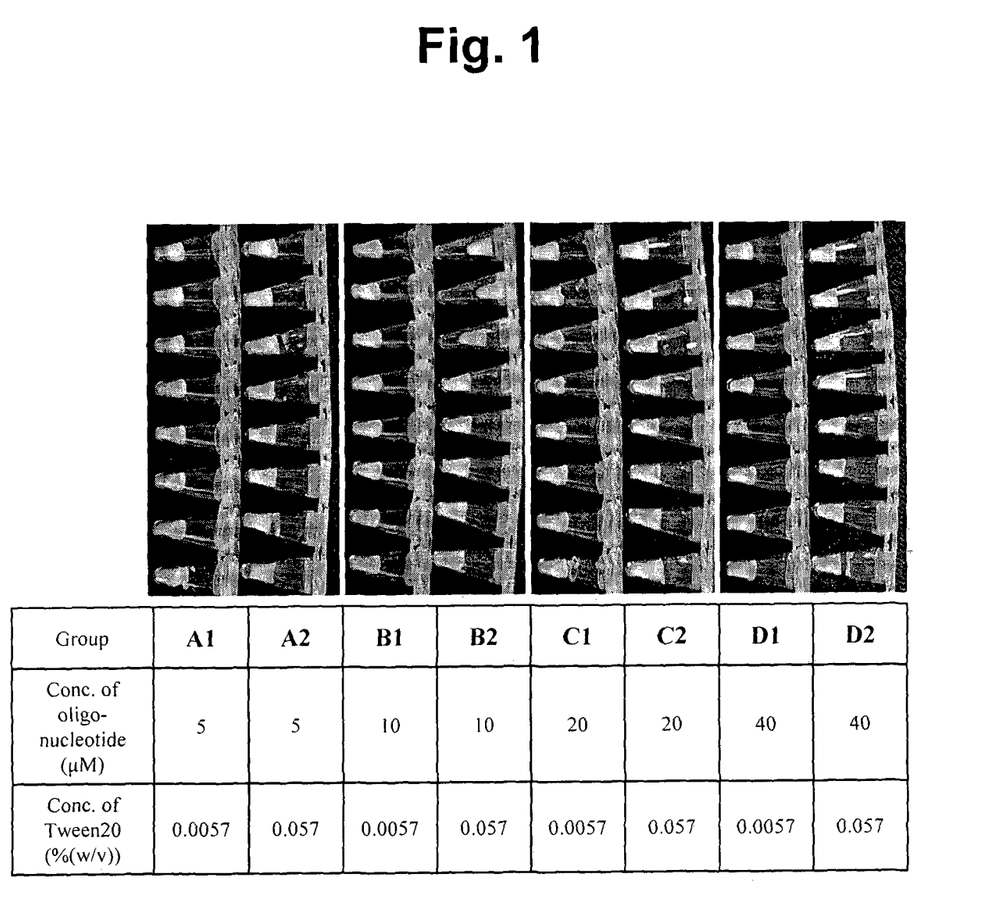
FIG. 1 represents lyophilization results of the present formulations for lyophilization with varying oligonucleotide concentrations.

The appearances of the lyophilizates with different concentrations of oligonucleotide were observed. FIG. 1 represents observation results on forms of the lyophilizates with different concentrations of oligonucleotide. As shown in FIG. 1, the groups with 0.0057% (w/v) Tween 20 (A1, B1, C1 and D1) were observed to exhibit a transparent layer and cake shrinkage over all concentrations of oligonucleotides (5 µM, 10 µM, 20 µM and 40 µM). In contrast, the groups with 0.057% (w/v) Tween 20 (A2, B2, C2 and D2) was observed to exhibit good appearance of lyophilizate cake.

Therefore, these results urge us to reason that polysorbate is required in suitable concentrations to lyophilize compositions for multiple target nucleic acid sequence amplification reaction with high concentrated oligonucleotides.

Example 2: Preparation of Lyophilizates with Different Polysorbate Concentrations To elucidate whether concentrations of polysorbate affect lyophilization of formulation for lyophilization, the formulations for lyophilization were prepared with different polysorbate concentrations and lyophilized.

To the compositions for multiple target nucleic acid sequence amplification reaction containing oligonucleotides (TOM), Taq DNA polymerase, $MgCl_2$, dNTPs and Tris-HCl, the additive containing polysorbate (Tween 20), trehalose and polyethylene glycol was added, followed by mixing with water for preparing the formulations for lyophilization with the final volume of 30 µl. The preparation groups were divided to five groups depending on Tween 20 concentrations.

The prepared formulations for lyophilization comprising compositions for multiple target nucleic acid sequence amplification reaction were summarized in Table 2.

TABLE 2

| Formulation for lyophilzation | | A | B | C | D | E |
|---|---|---|---|---|---|---|
| Composition for amplification reaction | TOM (µM) | 10 | 10 | 10 | 10 | 10 |
| | Taq DNA polymerase (unit) | 1 | 1 | 1 | 1 | 1 |
| | $MgCl_2$ (mM) | 2.5 | 2.5 | 2.5 | 2.5 | 2.5 |
| | dNTP (mM) | 0.3 | 0.3 | 0.3 | 0.3 | 0.3 |
| | Tris-HCl (mM) | 20 | 20 | 20 | 20 | 20 |
| Additive | Tween20 (% (w/v)) | 0.0057 | 0.057 | 0.11 | 0.28 | 0.57 |
| | Trehalose (% (w/v)) | 18.15 | 18.15 | 18.15 | 18.15 | 18.15 |
| | Polyethylene glycol (% (w/v)) | 1.65 | 1.65 | 1.65 | 1.65 | 1.65 |
| Proportion of Tween20 based on 1 µM TOM (% (w/v)) | | 0.00057 | 0.0057 | 0.011 | 0.028 | 0.057 |

The prepared formulations for lyophilization were lyophilized in the same manner as Example 1.

Figure 2:
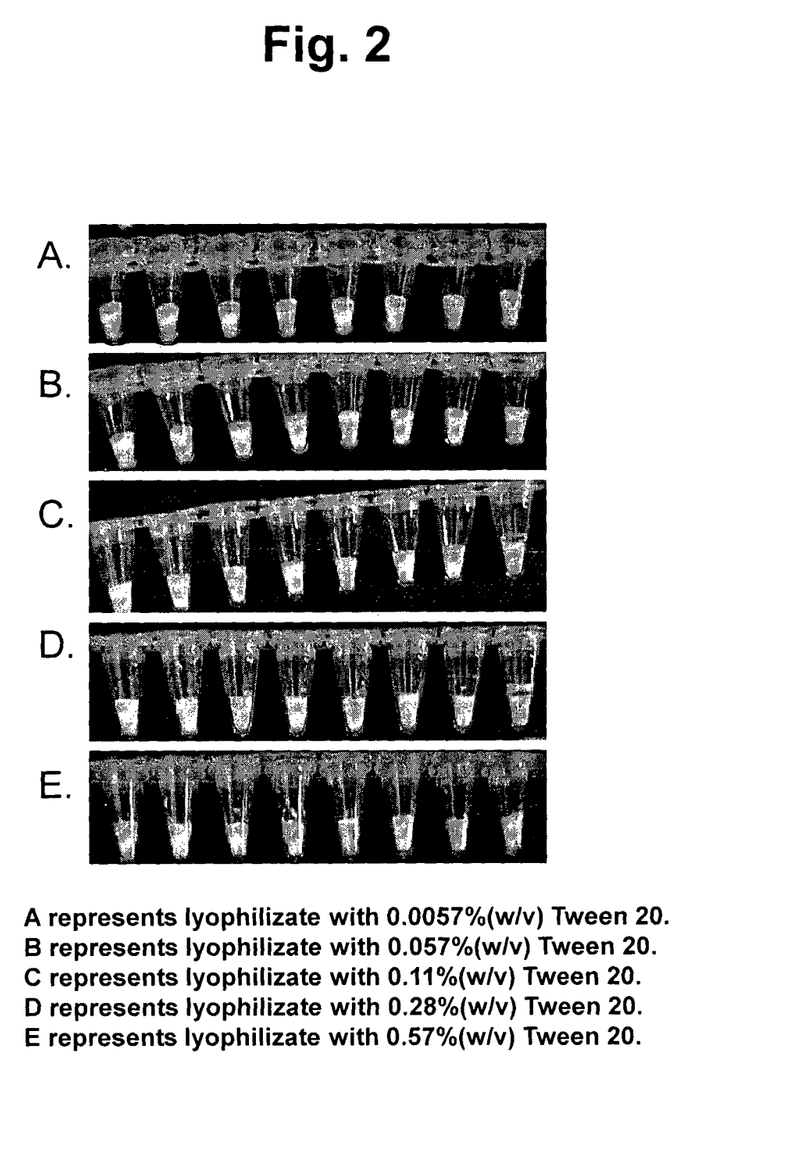
FIG. 2 represents lyophilization results of the present formulations for lyophilization with varying polysorbate (Tween 20) concentrations.

The appearances of the lyophilizates with different polysorbate concentrations were observed. FIG. 2 represents observation results on forms of the lyophilizates with different polysorbate concentrations. As shown in FIG. 2, the groups with Tween 20 of not less than 0.057% (w/v) (B-E) were observed to exhibit typical lyophilizate cake formation. Unlikely, the group with 0.0057% (w/v) Tween 20 (A) was observed to exhibit a transparent layer at a lower portion of lyophilizate cakes (see the circle lines of FIG. 2). Furthermore, while the group with 0.57% (w/v) Tween 20 (E) was shown to normally form lyophilizate cake, the lyophilizate cakes formed was very likely to be brittle.

These results would address that when polysorbate is contained in sufficient concentrations, lyophilization of the compositions for multiple target nucleic acid sequence amplification reaction are able to form cakes with a preferable manner.

Example 3: Analysis of Influences of Drying Time on Lyophilizates

For analyzing influences of drying time on lyophilizates, lyophilizates were prepared with varying time of the primary drying.

The formulations for lyophilization were prepared in the same manner as Groups A, B and C in Example 2. The formulations for lyophilization thus prepared were divided into two groups according to the primary drying time and then lyophilized with the following conditions:

TABLE 3

| | 48-hr Group | | 60-hr Group | |
|---|---|---|---|---|
| Steps | Temp(° C.) | Time(hr) | Temp(° C.) | Time(hr) |
| Freezing | −55 | 24 | −55 | 12 |
| Primary drying | −30 | 48 | −30 | 60 |
| Secondary drying | 20 | 0.5 | 20 | 2 |

For lyophilization, a pressure of 100 mTorr was applied to all groups.

Figure 3:
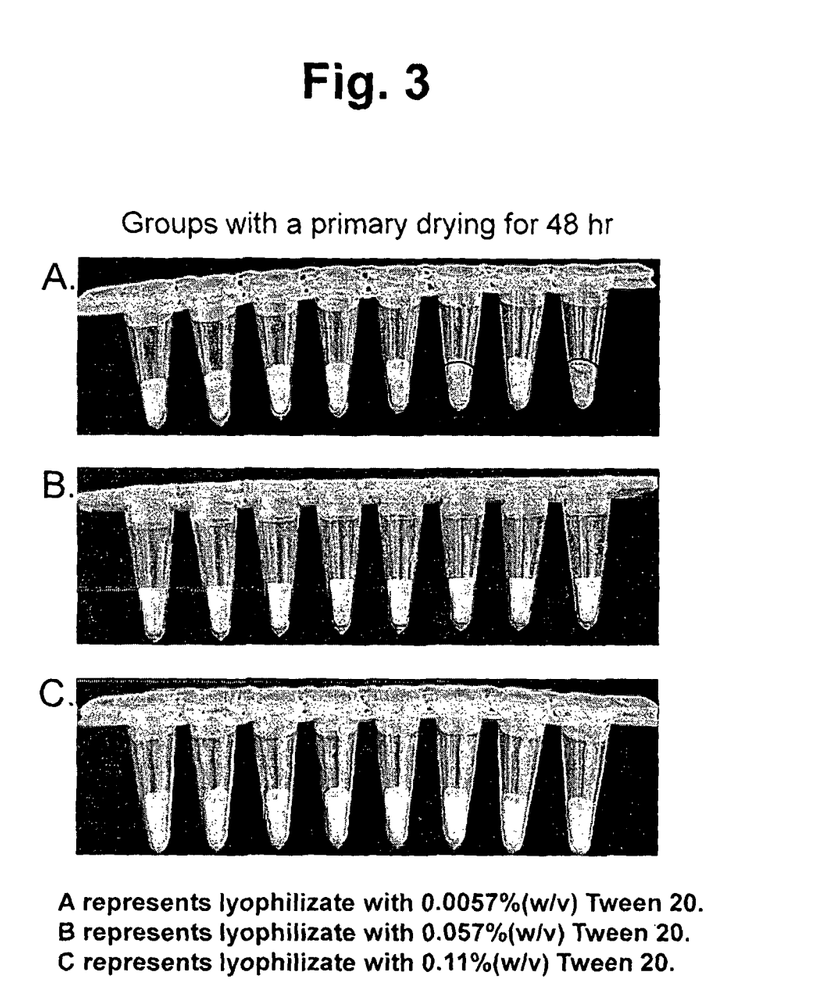
FIG. 3 represents results of lyophilization with a primary drying for 48 hr.

The appearances of the lyophilizates were observed. FIG. 3 represents observation results on forms of the lyophilizates prepared with 48-hr primary drying and FIG. 4 represents observation results on forms of the lyophilizates prepared with 60-hr primary drying.

As shown in FIG. 3, when a primary drying was carried out for 48 hr, the groups with 0.057% (w/v) or 0.11% (w/v) Tween 20 were shown to excellently form lyophilizate cakes. The group with 0.0057% (w/v) Tween 20 was observed to exhibit a transparent layer in lyophilizate cakes (see the circle lines of FIG. 3) and even no lyophilizate cake formation of some tubes (see the circle lines of FIG. 3).

Figure 4:
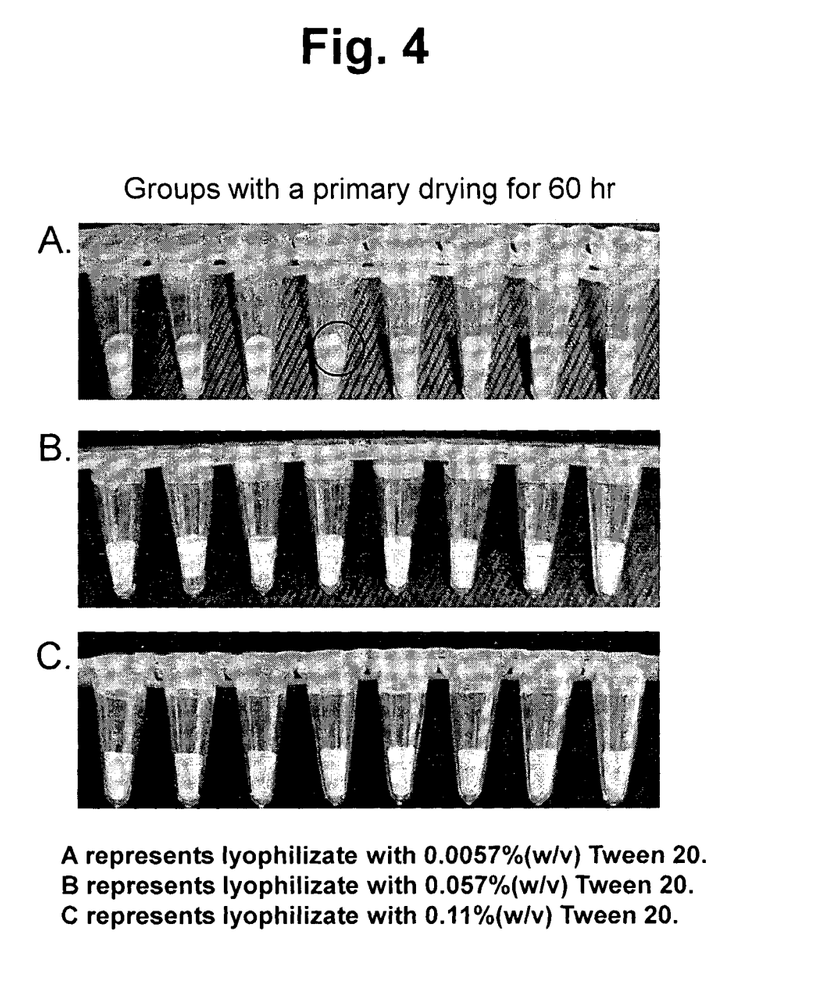
FIG. 4 represents results of lyophilization with a primary drying for 60 hr.

When the time for a primary drying was extended to 60 hr, the group with 0.0057% (w/v) Tween 20 was observed to exhibit a better appearance of lyophilizate cakes than 48-hr primary drying but its portion (a few tubes) to exhibit a transparent layer at a lower portion of lyophilizate cakes (see the circle lines of FIG. 4). The groups with 0.057% (w/v) or 0.11% (w/v) Tween 20 were shown to excellently form lyophilizate cakes as those of 48-hr primary drying.

Based on these results, it would be appreciated that a sufficient amount of polysorbate assures successful lyophilizate cake formation of the formulations for lyophilization with high concentrated oligonucleotides and a sufficient time for the primary drying allows to elevate quality of lyophilized products.

Example 4: Evaluation of Performance of Lyophilizates

We evaluated whether the lyophilizates of compositions for multiple target nucleic acid sequence amplification reaction prepared in Example 3 maintains their detection capacity for pathogens of interest. Following reconstitution of the lyophilizates of compositions for multiple target nucleic acid sequence amplification reaction with distilled water, pathogen DNA templates were incubated with the reconstituted resultant and reactions were undertaken to detect signals. The detected signals were compared with experiments using a liquid product of reaction mixture. The liquid product is a conventional liquid formulation that detects the same target analyte with the present lyophilizates.

show fluorescent signal intensity better than that from the lyophilized group containing 0.0057% (w/v) Tween 20 (denoted as 1X_lyophilizates). In particular, when the concentrations of the pathogen DNA templates were reduced ($10^2$ and $10^1$ copies/reaction), the fluorescent signal intensities of 10X_lyophilizates were analyzed to be considerably maintained and those of 1X_lyophilizates to be sharply decreased.

Those results demonstrate that the lyophilizates of the present invention maintain a performance potential to detect pathogens by real-time PCR.

TABLE 4

| Conc. of DNA (copy/rxn) | 1X_lyophilizates | | 10X_lyophilizates | | Liquid | 1X_lyophilizates | | 10X_lyophilizates | | Liquid |
|---|---|---|---|---|---|---|---|---|---|---|
| | Average | Ratio | Average | Ratio | Average | Average | Ratio | Average | Ratio | Average |
| | *Ureaplasma urealyticum* | | | | | *Ureaplasma parvum* | | | | |
| $10^3$ | 237.1 | 0.75 | 264.6 | 0.84 | 316.6 | 262.8 | 0.76 | 292.7 | 0.85 | 345.7 |
| $10^2$ | 159.3 | 0.48 | 233.8 | 0.71 | 329.2 | 184.1 | 0.53 | 308.1 | 0.88 | 350.3 |
| $10^1$ | 111.3 | 0.32 | 233.1 | 0.67 | 349.9 | 119.6 | 0.34 | 273.1 | 0.77 | 356.4 |
| | *Mycoplasma genitalium* | | | | | *Mycoplasma hominis* | | | | |
| $10^3$ | 188.4 | 0.76 | 212.2 | 0.85 | 249.4 | 124.6 | 1.20 | 148.6 | 1.43 | 104.1 |
| $10^2$ | 119.9 | 0.50 | 217.7 | 0.90 | 240.7 | 71.7 | 0.76 | 145 | 1.54 | 93.9 |
| $10^1$ | 113.4 | 0.51 | 218.5 | 0.98 | 222.2 | | 0.00 | 173.9 | 2.40 | 72.6 |
| | *Neisseria gonorrhoeae* | | | | | *Chlamydia trachomatis* | | | | |
| $10^3$ | 493.1 | 0.90 | 553.6 | 1.01 | 548.7 | 441.8 | 0.86 | 511.5 | 1.00 | 511.0 |
| $10^2$ | 379.3 | 0.70 | 576.5 | 1.06 | 543.1 | 314.3 | 0.64 | 535.1 | 1.08 | 494.1 |
| $10^1$ | 292.1 | 0.55 | 570.5 | 1.08 | 528.9 | 218.1 | 0.46 | 521.5 | 1.10 | 474.8 |
| | Internal control | | | | | *Trichomonas vaginalis* | | | | |
| $10^3$ | 173 | 0.69 | 217.7 | 0.87 | 250.6 | 230.3 | 0.79 | 283 | 0.97 | 292.9 |
| $10^2$ | 113.4 | 0.50 | 207.3 | 0.91 | 228.0 | 152.5 | 0.58 | 254.5 | 0.97 | 263.6 |
| $10^1$ | 114.2 | 0.56 | 175.8 | 0.86 | 204.3 | 60.5 | 0.25 | 160.8 | 0.67 | 240.5 |

1X_lyophilizates: lyophilizates containing 0.0057% (w/v) Tween 20;
10X_lyophilizates: lyophilizates containing 0.057% (w/v) Tween 20;
Liquid: non-lyophilized conventional liquid formulation containing the same components and concentrations as those of lyophilizates;
Average: Averaged fluorescent intensity;
Ratio: ratio of fluorescent signal intensity of a lyophilizate group to that of a liquid group.

Among the lyophilizates prepared in Example 3, those with 0.0057% (w/v) or 0.057% (w/v) Tween 20 were used for experiments. The samples were divided to three groups comprising 10 copies, 100 copies and 1000 copies of pathogen DNA templates to be detected, respectively.

Five μl of plasmid DNA mixture (including seven sex-transmitted pathogen genes and internal control) were added to a PCR tube containing a lyophilizate and its volume was adjusted to 30 μl using RNase-free water. The PCR tube was placed on CFX96™ Real-time PCR System (Bio-Rad, USA). Uracil-DNA glycosylase (UDG) system was used for real-time PCR. Real-time PCR was performed for 4 min at 50° C. and for 15 min at 95° C. for denaturation (for UDG system), and then by 50 amplification cycles of 30 sec at 95° C., 60 sec at 60° C. and 30 sec at 72° C. For real-time signal detection, temperatures were elevated from 55° C. to 85° C. by 0.5° C. per 5 sec after the 50$^{th}$ amplification cycle.

As a control sample, a non-lyophilized liquid formulation containing the same components and concentrations as Group B of Example 2 was used. The control sample contained the same DNA template as described above was subjected to real-time PCR and signal detection under the same conditions as described above.

Table 4 summarizes signal intensities of each experimental group. The lyophilized group containing 0.057% (w/v) Tween 20 (denoted as 10X_lyophilizates) was analyzed to Example 5: Analysis of Properties of Lyophilizates To verify whether lyophilizates prepared by the present invention were suitable for diagnosis, the sensitivity and specificity of the lyophilizates were analyzed and compared with liquid formulation.

The formulations for lyophilization containing 10 μM TOM, 1 unit of Taq DNA polymerase, 2.5 mM $MgCl_2$, 0.3 mM dNTPs, 20 mM Tris-HCl, 0.057% (w/v) Tween 20, 18.3% (w/v) trehalose and 1.65% (w/v) polyethylene glycol were prepared with the final volume of 30 μl.

The preparation of the formulations for lyophilization and lyophilization process are the same as those of 60 hr-group in Example 3.

Analysis of Sensitivity

The analysis of sensitivity was carried out by evaluating limit of detection (LoD) of lyophilizates of compositions for multiple target nucleic acid sequence amplification reaction. Plasmid DNAs carrying each of seven sex-transmitted pathogen genes were employed. NG and CT each had two target regions (NG-NGp, NGm, CT-CTc and CTg).

The copy numbers of the pathogen DNAs in DNA samples were calculated by absorbance measurements using a spectrophotometer and the DNA samples were serially diluted to $10^5$-$10^1$ with 50 mM Tris-EDTA (pH 8.0). The diluted DNA samples were detected by using the lyophilizates of compositions for multiple target nucleic acid sequence amplification reaction. The detection of each gene was repeated eight times.

Table 5 is results of sensitivity analysis of the lyophilizates. As indicated in Table 5, the lyophilizates of compositions for multiple target nucleic acid sequence amplification reaction permitted to successfully detect DNA samples of up to 50 copies/reaction.

TABLE 5

| Copies/rxn | Target | | | | | | | | | |
|---|---|---|---|---|---|---|---|---|---|---|
| | UU | UP | MG | MH | NGp | NGm | CTc | CTg | TV | IC |
| $10^5$ | 8/8 | 8/8 | 8/8 | 8/8 | 8/8 | 8/8 | 8/8 | 8/8 | 8/8 | 8/8 |
| $10^3$ | 8/8 | 8/8 | 8/8 | 8/8 | 8/8 | 8/8 | 8/8 | 8/8 | 8/8 | 8/8 |
| $10^2$ | 8/8 | 8/8 | 8/8 | 8/8 | 8/8 | 8/8 | 8/8 | 8/8 | 8/8 | 8/8 |
| 50 | 8/8 | 8/8 | 8/8 | 8/8 | 8/8 | 8/8 | 8/8 | 8/8 | 8/8 | 8/8 |
| 10 | 2/8 | 4/8 | 6/8 | 3/8 | 7/8 | 6/8 | 5/8 | 5/8 | 3/8 | 7/8 |

Chlamydia trachomatis (CT);
Neisseria gonorrhoeae (NG);
Trichomonas vaginalis (TV);
Mycoplasma hominis (MH);
Mycoplasma genitalium (MG);
Ureaplasma urealyticum (UU);
Ureaplasma parvum (UP);
IC: internal control.

Analysis of Specificity

To analyze the specificity of the present lyophilizates, pathogens other than the target pathogens were used.

Nucleic acids were extracted from thirty-seven bacterial and viral pathogens other than the target pathogens. Following reconstitution of the present lyophilizates with distilled water, the thirty-seven nucleic acids were added to hydrated lyophilizates to become $10^4$ copies/reaction and water was added to the final volume of 30 µl. The reactions were carried out in the same manner as those of Example 4 and positive cases were observed. The signal detection for each gene was repeated twice.

Table 6 is results of specificity analysis of the lyophilizates. As indicated in Table 6, thirty-seven bacterial and viral pathogens other than the target pathogens were not detected by the lyophilizates of the present invention.

TABLE 6

| No. | Organism | No. of positive |
|---|---|---|
| 1 | Acinetobacter baumannii | 0/2 |
| 2 | Acinetobacter schindleri | 0/2 |
| 3 | Atopobium vaginae | 0/2 |
| 4 | Bacteroides fragilis | 0/2 |
| 5 | Candida albicans | 0/2 |
| 6 | Candida dubliniensis | 0/2 |
| 7 | Candida glabrata | 0/2 |
| 8 | Candida parapsilosis | 0/2 |
| 9 | Candida tropicalis | 0/2 |
| 10 | Chlamydophila pneumoniae | 0/2 |
| 11 | Clostridium difficile | 0/2 |
| 12 | Clostridium perfringens | 0/2 |
| 13 | Cytomegalovirus (CMV) | 0/2 |
| 14 | Enterococcus avium | 0/2 |
| 15 | Epstein Barr Virus | 0/2 |
| 16 | Escherichia coli | 0/2 |
| 17 | Gardnerella vaginalis | 0/2 |
| 18 | Haemophilus ducreyi | 0/2 |
| 19 | Haemophilus influenza | 0/2 |
| 20 | Hepatitis B virus (HBV) | 0/2 |
| 21 | Hepatitis C virus (HCV) | 0/2 |
| 22 | HSV1 | 0/2 |
| 23 | HSV2 | 0/2 |
| 24 | Human Papilloma Virus 16 | 0/2 |
| 25 | Human Papilloma Virus 18 | 0/2 |
| 26 | Neisseria cinerea | 0/2 |
| 27 | Neisseria meningitidis | 0/2 |
| 28 | Neisseria mucosa | 0/2 |
| 29 | Neisseria perflava | 0/2 |
| 30 | Neisseria sicca | 0/2 |
| 31 | Salmonella enteritidis | 0/2 |
| 32 | Staphylococcus aureus | 0/2 |
| 33 | Streptococcus agalactiae | 0/2 |
| 34 | Streptococcus pneumoniae | 0/2 |
| 35 | Vibrio parahaemolyticus | 0/2 |
| 36 | Yersinia enterocolitica | 0/2 |
| 37 | Pseudomonas aeruginosa | 0/2 |
| — | — | — |

Analysis of Equivalency of Lyophilizates to Liquid Form

We analyzed whether the present lyophilizates exhibited equivalent performance to conventional liquid formulation.

The conventional liquid formulation is a conventional diagnostics product in a liquid formulation that detects the same target analyte with the present lyophilizates.

DNA templates were extracted from 184 genital swap samples using Qiagen DNA mini kit (Gaithersburg, USA). Real-time PCR and signal detection were performed by the same manner as described above.

As indicated in Table 7, the lyophilizates of the present invention exhibited the sensitivity of 94.3% to 100% and the specificity of 99.4% to 100% compared with the conventional liquid form, addressing that the present lyophilizates have equivalent performance capacity to the conventional liquid formulation.

TABLE 7

| | | STI-7 Reference method (AnyplexII STI-7) Target | | | | | | | | |
|---|---|---|---|---|---|---|---|---|---|---|
| | | UU | | | UP | | | MG | | |
| | | Pos | Neg | Total | Pos | Neg | Total | Pos | Neg | Total |
| Lyophilizate | Pos | 39 | 0 | 39 | 97 | 0 | 97 | 8 | 1 | 9 |
| | Neg | 0 | 145 | 145 | 0 | 87 | 87 | 0 | 175 | 175 |
| | Total | 39 | 145 | 184 | 97 | 87 | 184 | 8 | 176 | 184 |
| | Sensitivity | 100% | | | 100% | | | 100% | | |
| | Specificity | 100% | | | 100% | | | 99.43% | | |

TABLE 7-continued

| | | STI-7 Reference method (AnyplexII STI-7) Target | | | | | | | | |
|---|---|---|---|---|---|---|---|---|---|---|
| | | MH | | | CT | | | TV | | |
| | | Pos | Neg | Total | Pos | Neg | Total | Pos | Neg | Total |
| Lyophilizate | Pos | 33 | 0 | 33 | 10 | 0 | 10 | 2 | 0 | 2 |
| | Neg | 2 | 149 | 151 | 0 | 174 | 174 | 0 | 182 | 182 |
| | Total | 35 | 149 | 184 | 10 | 174 | 184 | 2 | 182 | 184 |
| | Sensitivity | | 94.29% | | | 100% | | | 100% | |
| | Specificity | | 100% | | | 100% | | | 100% | |

Pos: positive case;
Neg: negative case

Analysis of Stability of Lyophllizates

We analyzed stability of the present lyophilizates in such a manner that 8-strip PCR tubes containing the present lyophilizates were sealed into aluminum pouch together with humectants and stored for a certain period of time followed by analyzing their detection performance. The storage was performed at 4° C. and the analysis of the detection performance was performed on 0 month, 3 month, 6 month, is 9 month and 12 month after the storage.

The lyophilizates were rehydrated and incubated with pathogen DNA templates (100 copies/reaction). The generated signal was analyzed in such a manner that a melt peak height was maintained on or above a predetermined reference height.

Table 8 summarizes analysis results of stability tests of the present lyophilizates. The results are average values of duplicated tests. As represented in Table 8, the present lyophilizates maintains their performance capacity over the reference activity until 12 month after storage.

TABLE 8

| | | Target | | | | | | | |
|---|---|---|---|---|---|---|---|---|---|
| | | UU | UP | MG | MH | NG | CT | IC | TV |
| Reference height (melt peak) | | 120 | 140 | 100 | 50 | 200 | 180 | 110 | 90 |
| Storage term (month) | 0 | 265.3 | 308.3 | 194.3 | 78.5 | 437.3 | 373.0 | 135.4 | 122.2 |
| | 3 | 239.9 | 271.0 | 193.3 | 165.0 | 459.4 | 407.4 | 145.2 | 131.9 |
| | 6 | 171.9 | 215.2 | 168.1 | 228.2 | 419.5 | 347.1 | 125.6 | 114.9 |
| | 9 | 216.0 | 239.8 | 162.7 | 236.3 | 412.3 | 363.0 | 124.6 | 95.9 |
| | 12 | 181.3 | 231.7 | 159.5 | 161.06 | 401.7 | 328.1 | 138.3 | 100.7 |

The analysis results of Example 5 address that the lyophilizates prepared by the present invention exhibits excellent properties in terms of both sensitivity and specificity, equivalent performance capacity to conventional liquid formulation and furthermore remarkable storage stability. Accordingly, the lyophilizates prepared by the present invention would be very useful in diagnosis.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for lyophilizing a composition for multiple target nucleic acid sequence amplification reaction, comprising:

(a) preparing a formulation comprising (i) the composition for multiple target nucleic acid sequence amplification reaction and (ii) an additive containing polysorbate, trehalose, and polyethylene glycol, wherein the formulation comprises oligonucleotides in an amount not less than 2 μM and the formulation comprises polysorbate in an amount of 0.0012-0.5% (w/v) based on 1 μM oligonucleotides; and
   (b) lyophilizing the formulation.

2. The method according to claim 1, wherein the composition for multiple target nucleic acid sequence amplification reaction comprises (i) oligonucleotides containing at least three primer pairs for amplifying at least three target nucleic acid sequences and (ii) an enzyme.

3. The method according to claim 2, wherein the enzyme is selected from the group consisting of nucleic acid polymerase, nucleolytic enzyme, nucleic acid polymerase having nucleolytic activity and a combination thereof.

4. The method according to claim 1, wherein the polysorbate is polysorbate 20.

5. The method according to claim 1, wherein the step (b) comprises:

(i) freezing the formulation prepared in the step (a) at −20°C. to −80°C. for 1 hr to 96 hr;
   (ii) performing a primary drying of the resultant of the step (i) at −15°C. to −60°C. for 6 hr to 96 hr; and
   (iii) performing a secondary drying of the resultant of the step (ii) at 0°C. to 100°C. for 0.5 hr. to 48 hr.

6. The method according to claim 5, wherein the primary drying of the step (ii) is performed at −25°C. to −35°C. for 50 hr to 72 hr.

7. A lyophilizate of a composition for multiple target nucleic acid sequence amplification reaction prepared by the method of claim 1.

8. A formulation for lyophilization, comprising a composition for multiple target nucleic acid sequence amplification reaction and an additive containing polysorbate, trehalose and polyethylene glycol; wherein the formulation comprises oligonucleotides in amount of not less than 2 μM and wherein the formulation comprises polysorbate in an amount of 0.0012-0.5% (w/v) based on 1 μM oligonucleotides.

9. The formulation for lyophilization according to claim 8, wherein the composition for multiple target nucleic acid sequence amplification reaction comprises oligonucleotides containing at least three primer pairs for amplifying at least three target nucleic acid sequences and an enzyme.

10. The formulation for lyophilization according to claim 9, wherein the enzyme is selected from the group consisting of nucleic acid polymerase, nucleolytic enzyme, nucleic acid polymerase having nucleolytic activity and a combination thereof.

* * * * *